(12) United States Patent
Malchow et al.

(10) Patent No.: US 6,837,961 B2
(45) Date of Patent: Jan. 4, 2005

(54) METHOD OF MAKING TEAR-RESISTANT ADHESIVE/COMBINATION BOND PATTERN

(75) Inventors: Gregory Lynn Malchow, Oshkosh, WI (US); Daniel Hoo, Appleton, WI (US); Timothy James Blenke, Neenah, WI (US); Jeffry Jon Radke, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 31 days.

(21) Appl. No.: 10/290,836

(22) Filed: Nov. 8, 2002

(65) Prior Publication Data

US 2003/0069554 A1 Apr. 10, 2003

Related U.S. Application Data

(62) Division of application No. 09/944,242, filed on Aug. 30, 2001, now Pat. No. 6,652,501.
(60) Provisional application No. 60/229,189, filed on Aug. 30, 2000.
(51) Int. Cl.$^7$ ............................................. B32B 31/26
(52) U.S. Cl. .................... 156/290; 156/73.1; 428/198; 428/201; 604/385.01; 604/396
(58) Field of Search .................. 156/196, 73.1, 156/290–291; 428/102–103, 195.1, 196, 198, 201; 604/385.01, 396; 53/477

(56) References Cited

U.S. PATENT DOCUMENTS 4,493,868 A   1/1985   Meitner ...................... 428/171
5,547,747 A   8/1996   Trokhan et al.
5,624,420 A * 4/1997   Bridges et al. ............. 604/365
D412,508 S    8/1999   Witsken ..................... D15/126
5,964,742 A   10/1999  McCormack et al.
6,387,083 B1  5/2002   Suzuki
6,443,931 B1  9/2002   Kurata et al.

FOREIGN PATENT DOCUMENTS

| DE | 30 09 465 A1 | 9/1981  | ............ D06N/7/00  |
| EP | 0 346 928 A2 | 12/1989 | ............ A61F/13/18 |
| EP | 0 657 153 A2 | 6/1995  | ............ A61F/13/15 |
| EP | 0 677 284 A1 | 10/1995 | ............ A61F/13/15 |
| EP | 0 800 808 A1 | 10/1997 | ............ A61F/13/62 |
| EP | 0 803 602 A1 | 10/1997 | ............ D04H/3/16  |
| GB | 1 332 037    | 10/1973 | ............ B29C/27/02 |
| WO | WO 98/02610  | 1/1998  | ............ D04H/13/00 |
| WO | WO 98/27904  | 7/1998  |                         |
| WO | WO 99/14262  | 3/1999  | ............ C08J/5/18  |

* cited by examiner

Primary Examiner—Jeff H. Aftergut
Assistant Examiner—Jessica Rossi
(74) Attorney, Agent, or Firm—Kimberly-Clark Worldwide, Inc.

(57) ABSTRACT

Bonded composites, absorbent articles comprising such bonded composites, and processes for bonding thin-section elements. The bonded composite has first and second thin-section elements bonded to each other, at least in part by bond elements and at least in part by adherent material. The adherent material is disposed between the first and second thin-section elements proximate and about the bond elements. The adherent material, at least in part, bonds the thin-section elements to each other at loci of the adherent material. The bond patterns are arranged and configured to preferentially direct stresses imposed on the bond pattern, inwardly into the interior of the bond pattern for distribution, dissipation, and termination.

3 Claims, 11 Drawing Sheets

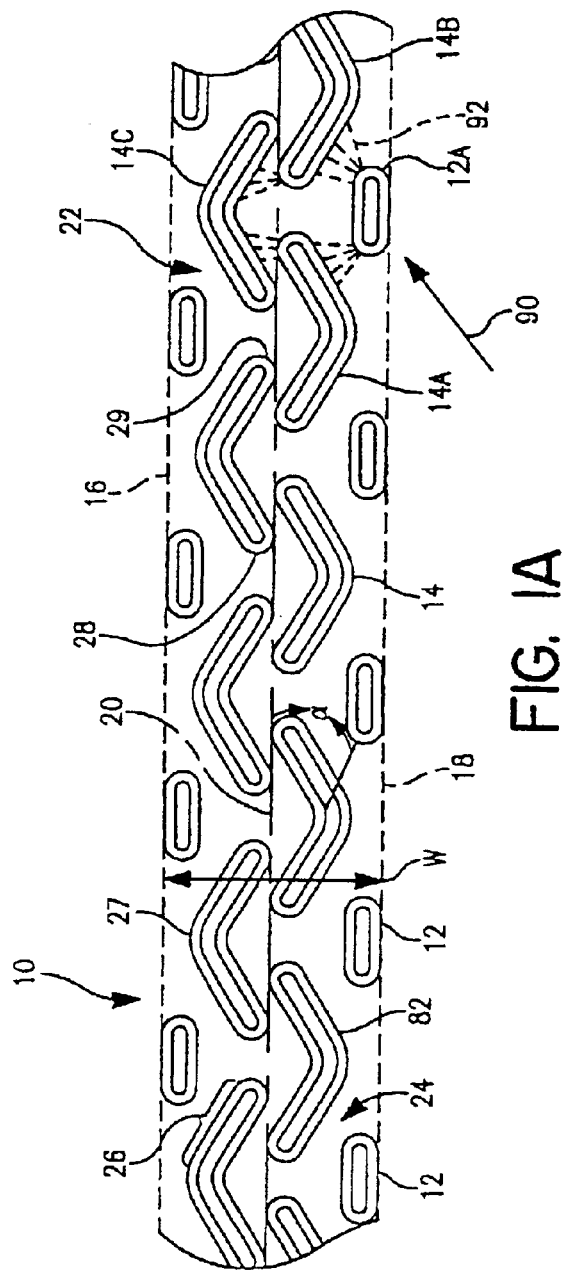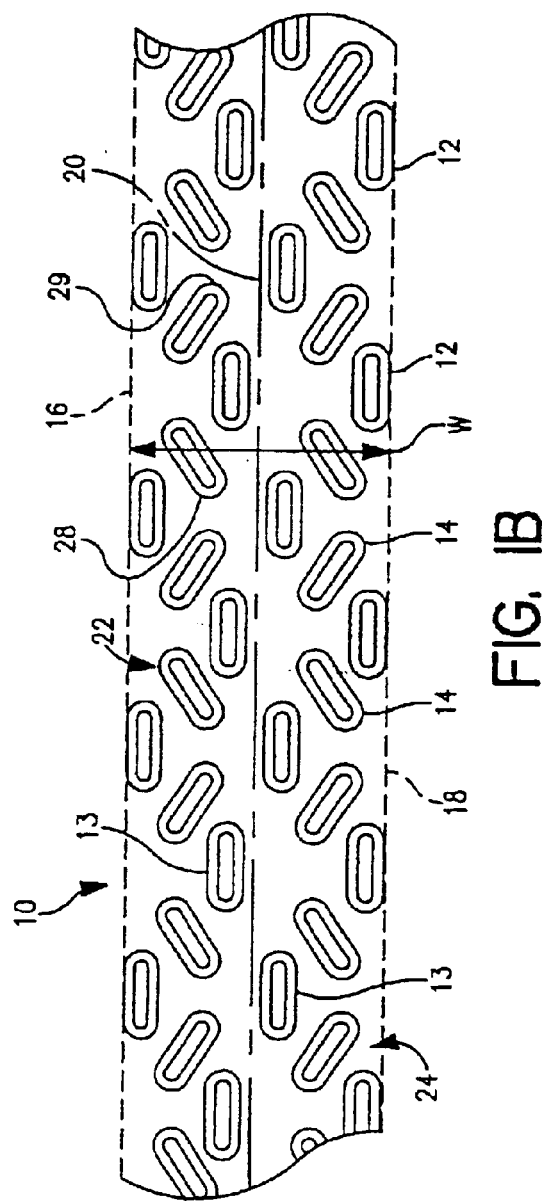
FIG. 1A
FIG. 1B

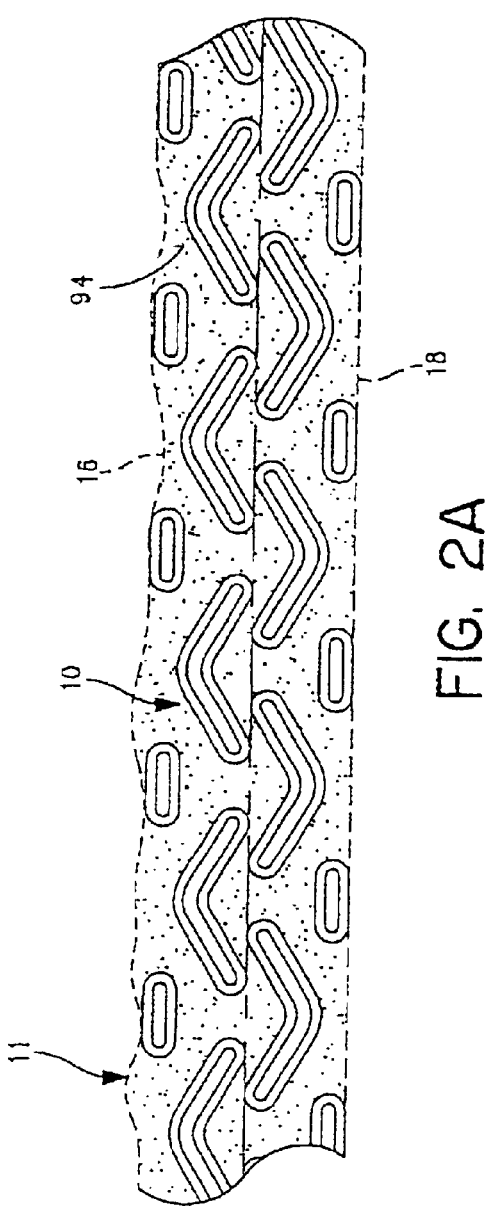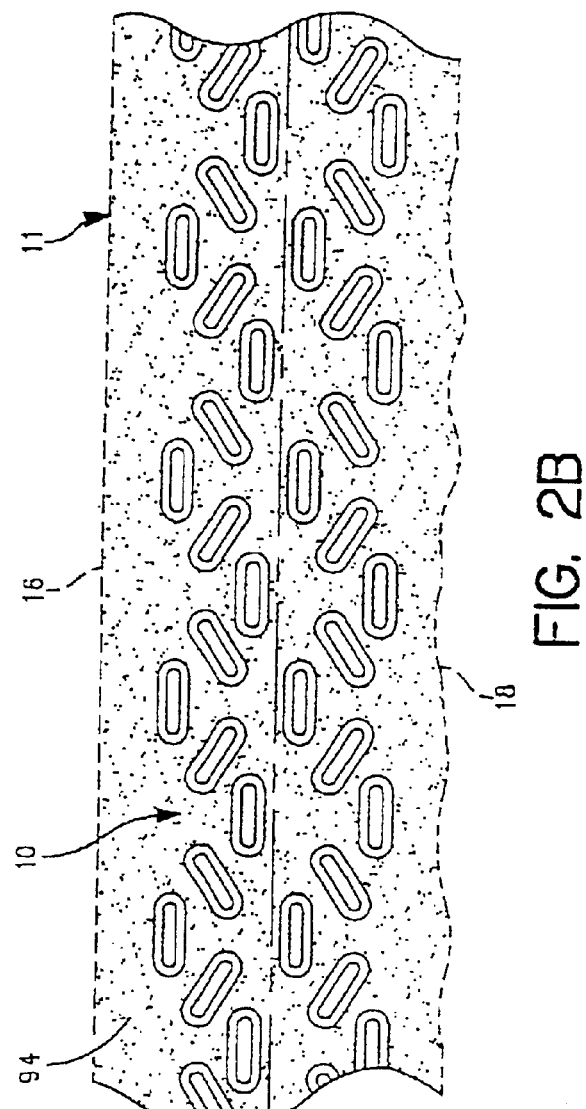

|    | A     | B     | C     | D     |
|----|-------|-------|-------|-------|
| 1  | 0.030 | 0.030 |       | 0.060 |
| 2  | 0.030 | 0.030 |       | 0.060 |
| 3  | 0.030 | 0.031 |       | 0.061 |
| 4  | 0.030 | 0.032 |       | 0.062 |
| 5  | 0.030 | 0.033 |       | 0.063 |
| 6  | 0.030 | 0.034 |       | 0.064 |
| 7  | 0.030 | 0.035 |       | 0.065 |
| 8  | 0.030 | 0.035 |       | 0.065 |
| 9  | 0.014 | 0.019 | 0.035 | 0.068 |
| 10 | 0.030 | 0.035 |       | 0.064 |
| 11 | 0.034 | 0.035 |       | 0.069 |
| 12 | 0.035 | 0.035 |       | 0.069 |
| 13 | 0.035 | 0.035 |       | 0.069 |
| 14 | 0.035 | 0.035 |       | 0.069 |
| 15 | 0.035 | 0.035 |       | 0.069 |
| 16 | 0.035 | 0.035 |       | 0.069 |
| 17 | 0.035 | 0.035 |       | 0.069 |
| 18 | 0.035 | 0.035 |       | 0.069 |
| 19 | 0.035 | 0.035 |       | 0.069 |
| 20 | 0.035 | 0.035 |       | 0.069 |
| 21 | 0.035 | 0.033 |       | 0.067 |
| 22 | 0.035 | 0.026 |       | 0.060 |
| 23 | 0.035 | 0.026 |       | 0.061 |
| 24 | 0.035 | 0.030 |       | 0.065 |
| 25 | 0.035 | 0.030 |       | 0.065 |
| 26 | 0.034 | 0.030 |       | 0.064 |
| 27 | 0.033 | 0.030 |       | 0.063 |
| 28 | 0.031 | 0.030 |       | 0.061 |
| 29 | 0.030 | 0.030 |       | 0.060 |
| 30 | 0.030 | 0.030 |       | 0.060 |
| 31 | 0.030 | 0.030 |       | 0.060 |
| 32 | 0.030 | 0.030 |       | 0.060 |
| 33 | 0.031 | 0.030 |       | 0.061 |
| 34 | 0.033 | 0.030 |       | 0.063 |
| 35 | 0.034 | 0.030 |       | 0.064 |
| 36 | 0.035 | 0.030 |       | 0.065 |
| 37 | 0.035 | 0.030 |       | 0.065 |
| 38 | 0.035 | 0.027 |       | 0.061 |
| 39 | 0.035 | 0.026 |       | 0.060 |
| 40 | 0.035 | 0.033 |       | 0.067 |
| 41 | 0.035 | 0.035 |       | 0.069 |
| 42 | 0.035 | 0.035 |       | 0.069 |
| 43 | 0.035 | 0.035 |       | 0.069 |
| 44 | 0.035 | 0.035 |       | 0.069 |
| 45 | 0.035 | 0.035 |       | 0.069 |
| 46 | 0.035 | 0.035 |       | 0.069 |
| 47 | 0.035 | 0.035 |       | 0.069 |
| 48 | 0.035 | 0.035 |       | 0.069 |
| 49 | 0.035 | 0.035 |       | 0.069 |
| 50 | 0.034 | 0.035 |       | 0.069 |
| 51 | 0.030 | 0.035 |       | 0.064 |
| 52 | 0.014 | 0.019 | 0.035 | 0.068 |
| 53 | 0.028 | 0.035 |       | 0.063 |
| 54 | 0.030 | 0.035 |       | 0.065 |
| 55 | 0.030 | 0.034 |       | 0.064 |
| 56 | 0.030 | 0.033 |       | 0.063 |
| 57 | 0.030 | 0.032 |       | 0.062 |
| 58 | 0.030 | 0.031 |       | 0.061 |
| 59 | 0.030 | 0.030 |       | 0.060 |
| 60 | 0.030 | 0.030 |       | 0.060 |
| 61 |       |       |       | 0.064 |

FIG. 7

METHOD OF MAKING TEAR-RESISTANT ADHESIVE/COMBINATION BOND PATTERN

CROSS-REFERENCE TO RELATED APPLICATIONS

This application is a Divisional application claiming priority under 35 U.S.C. 120 to application Ser. No. 09/944,242 filed Aug. 30, 2001, now U.S. Pat. No. 6,652,501, which is incorporated herein by reference in its entirety, which claims priority to provisional application Ser. No. 60/229,189, filed Aug. 30, 2000.

BACKGROUND

The present invention relates to a bonded composite of a first thin-section element of sheet material and a second thin-section element bonded together by a bond pattern. More particularly, one of the contemplated applications for the present invention is in bonding outer cover and body side liner thin-section elements of absorbent articles to one another.

Absorbent articles have been known for a long time as personal care hygiene products. Absorbent articles find use, for example, as diapers, training pants, incontinence products, women's sanitary pads, and the like. Such absorbent articles are designed and constructed to absorb and store liquid bodily excretions such as urine, menstrual fluid, or blood. Women's sanitary pads are used, for example, to absorb the liquids excreted prior to, during, and after menstruation.

In absorbent articles, the portions of the article where different layers or components are bonded to each other tend to incur significant stress concentrations, and in absorbent articles using conventional bond patterns, tend to fracture at those bonded locations under such stresses. In conventional patterns used in absorbent articles, bond locations are disposed in uniform and crossing straight lines and straight rows of circular bond elements. The inventors herein have noted that such bond configuration has been found to enhance the probability that the absorbent article will tear and that the tear propagates along the side edge of the bond pattern. Tearing properties of such conventional patterns can be compared to perforated paper forms.

The problem addressed in the present invention is thus to provide a bonded composite demonstrating a bond pattern, and an absorbent article implementing the bond pattern, whereby the configuration of the bond pattern discourages the possibility for fracture of the bonded composite or absorbent article at the bond pattern.

The present invention solves this problem by means of the bonded composite as well as the absorbent article both disclosed and described in the independent claims. Additional advantageous embodiments of the absorbent article in accord with the invention and of the process in accordance with the invention arise from the dependent claims, the specification, and the drawings.

It is an object of this invention to reduce the ease of tearing of a bonded composite or absorbent article by introducing bonding patterns which discourage straight fracture of the bonded materials, and encourage dissipating an initially concentrated force within a substantial area of the bonding pattern.

SUMMARY

In a first family of embodiments, the invention comprehends a bonded composite. The bonded composite comprises, as a first thin-section element, a first layer of sheet material, a second thin-section element bonded, to the first thin-section element, at least in part by bond elements, and at least in part by adherent material. The adherent material is disposed between the first and second thin-section elements proximate and about ones of the bond elements. The adherent material, at least in part, bonds the thin-section elements to each other at loci of the adherent material. The combination of the adherent material and the bond elements defines a bond pattern.

The bond pattern has a pattern length, a pattern width represented by first and second side edges of the bond pattern, and a central longitudinal axis, typically centered on the bond elements. The side edges of the bond pattern and a corresponding pattern area between such side edges are defined generally by those areas of the respective thin-section elements which participate in absorbing and dissipating, by operation of the bond pattern, stresses received into the bond pattern from external sources.

The bond pattern has a pattern density defined generally by the fraction of the pattern area occupied by the bond elements. The bond elements proximate the side edges are spaced farther apart from each other than bond elements disposed more away from the side edges, thus creating a relatively less dense portion of the bond pattern proximate the side edges of the pattern, as measured by bond element fraction of the pattern area, and a relatively more dense portion of the bond pattern, as measured by bond element fraction of the pattern area, away from the side edges.

The bond pattern reflects application of force urging the first and second thin-section elements toward each other in face-to-face relationship to form an array of separate, distinct, and spaced elongate bond elements affixing the first and second thin-section elements to each other.

Bonds corresponding to the bond elements are activated by combined application of adherent material, pressure, and one of thermal energy or ultrasonic-frequency energy to at least one of the first and second thin-section elements.

In some embodiments, the bond pattern comprises, as ones of the bond elements, a first sub-array of longitudinally-oriented separate, distinct, and spaced stress receptor elements disposed along the length, and proximate the side edges of, the bond pattern. In such embodiments, the bond pattern can also comprise, as ones of the bond elements, a second sub-array of longitudinally-oriented separate, distinct, and spaced transfer and dissipation elements spaced along the length of the bond pattern, typically inwardly of the side edges of the bond pattern and generally inwardly of the stress receptor elements. Respective ones of the transfer and dissipation elements can have first ends disposed toward an interior of the bond pattern. The respective transfer and dissipation elements can extend to second ends adjacent the side edges of the bond pattern between respective ones of the stress receptor elements. The stress transfer and dissipation elements can direct stresses inwardly into the interior of the bond pattern, and can dissipate such stresses on the interior of the bond pattern.

In preferred embodiments, the adherent material comprises adhesive selected from the group consisting of contact adhesives, pressure sensitive adhesives, hot melt adhesives, two-part chemically activated adhesives, and mixtures and blends of such adherent materials.

The adherent material can be distributed and/or dispersed between the first and second thin-section elements as a result of the force being applied to the thin-section elements, such distribution and/or dispersal of the adherent material assisting in defining outer transverse edges of the adherent material in the bond pattern.

In preferred embodiments, at least one of the first thin-section element and the second thin-section element comprises polymeric material selected from the group consisting of polyolefins including polyethylenes and polypropylenes, polyesters, and polyamides, and copolymers, mixtures, and blends of such polymeric materials.

Generally, at least one of the first thin-section element and the second thin-section element comprises a fibrous web defining a multiplicity of randomly-spaced small openings extending from a major surface of the web into the interior of the web.

In some embodiments, the bond elements define the bond pattern in a repeating arrangement of pattern segments.

In some embodiments, outer edges of the adherent material define an adherent material pattern corresponding with at least about 50 percent of the pattern area of the bond pattern, preferably, with at least about 75 percent of the pattern area of the bond pattern, more preferably, with substantially all of the pattern area of the bond pattern.

In a second family of embodiments, the invention comprehends a bond pattern, reflecting application of force, which urges the first and second thin-section elements toward each other in face-to-face relationship to form an array of separate, distinct, and spaced elongate bond elements affixing the first and second thin-section elements to each other. Bonds corresponding to the bond elements are activated by a combined application of adherent material, pressure, and one of thermal energy or ultrasonic-frequency energy to at least one of the first and second thin-section elements. The adherent material is one or both distributed and dispersed between the first and second thin-section elements as a result of the force being applied to the thin-section elements. One or both of the distribution and dispersal of the adherent material assist in defining outer transverse edges of the adherent material in the bond pattern.

As ones of the bond elements, a first sub-array of longitudinally-oriented separate, distinct, and spaced stress receptor elements is disposed along the length, and proximate the side edges of, the bond pattern. A second sub-array of longitudinally-oriented separate, distinct, and spaced transfer and dissipation elements is spaced along the length of the bond pattern, preferably inwardly of the side edges of the bond pattern and preferably generally inwardly of the stress receptor elements. Respective transfer and dissipation elements have first ends disposed toward an interior of the bond pattern, and which extend to second ends adjacent the side edges of the bond pattern between respective ones of the stress receptor elements. The stress transfer and dissipation elements direct stresses inwardly into the interior of the bond pattern, and assist in dissipating such stresses on the interior of the bond pattern.

In a third family of embodiments, the invention comprehends as ones of the bond elements, a first sub-array of longitudinally-oriented separate and distinct stress receptor elements disposed proximate the side edges of the bond pattern, and spaced at first distances from each other along the length of the bond pattern, and a second sub-array of longitudinally-oriented separate and distinct transfer and dissipation elements preferably disposed inwardly of the side edges and preferably inwardly of the stress receptor elements, and at second distances from the stress receptor elements less than the spacing of respective ones of the stress receptor elements from each other.

In some embodiments, respective transfer and dissipation elements have first ends disposed toward an interior portion of the bond pattern, and extending to second ends adjacent the side edges of the bond pattern between respective ones of the stress receptor elements. In such embodiments, the transfer and dissipation elements direct stresses inwardly to the interior portion of the bond pattern, and assist in dissipating such stresses at the interior portion of the bond pattern.

In a fourth family of embodiments, the invention comprehends an absorbent article having a front portion and a rear portion, and a crotch portion extending between the front portion and the rear portion. The absorbent article comprises, as a first thin-section element, a first layer of sheet material, and a second thin-section element bonded to the first thin-section element, at least in part, by bond elements. The absorbent article further comprises adherent material disposed between the first and second thin-section elements proximate and about ones of the bond elements. The adherent material at least in part bonds the thin-section elements to each other at loci of the adherent material, the combination of the adherent material and the bond elements defining a bond pattern. The absorbent article also comprises an absorbent core disposed adjacent at least one of the first thin-section element and the second thin-section element.

In a fifth family of embodiments, the invention comprehends a process for bonding a first thin-section element and a second thin-section element to each other. The process comprises applying an adherent material to at least one of the first and second thin-section elements over at least part of an area of the respective thin-section material which is to be bonded. The process further comprises bringing the first and second thin-section elements together, including at the area to be bonded. Additionally, the process includes applying force urging the first and second thin-section elements toward and into surface-to-surface contact with each other including at the area to be bonded, and applying at least one of thermal energy or ultrasonic-frequency energy to at least one of the first and second thin-section elements in the area to be bonded, thereby forming an array of elongate bond elements and activating the adherent material proximate and generally about ones of the bond elements.

BRIEF DESCRIPTION OF THE DRAWINGS

FIGS. 1A, 1B, and 1C show plan views of representative bond patterns of this invention.

FIGS. 2A, 2B, 2C, 2D show plan views of representative bond patterns of this invention employing adherent material in addition to specific bond elements.

FIG. 7 is a table showing composite contact lengths of the bond elements across the width of the bond pattern, at spaced locations along the length of the bond pattern.

Figure 1C:
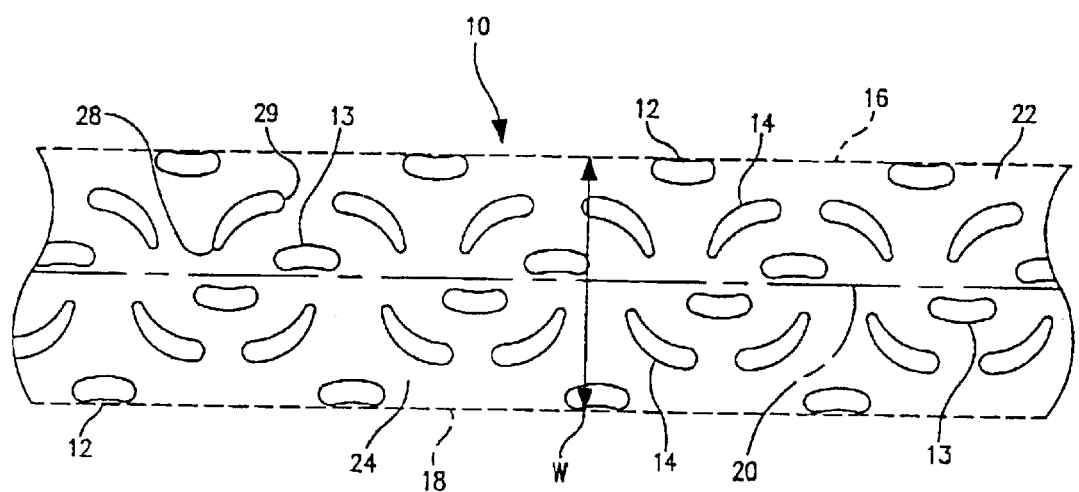

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

FIGS. 1A and 1B show preferable embodiments of bond pattern 10 of the invention, which is described more fully in application Ser. No. 09/651,042 filed Aug. 30, 2000, of common assignment herewith, and which is herein incorporated by reference in its entirety. Bond pattern 10 has a first side edge 16, a second side edge 18, and a central longitudinal axis 20 which divides the bond pattern 10, as defined by the bond elements, into a first opposing pattern combination 22 on a first side of axis 20 and a second opposing pattern combination 24 on an opposing second side of axis 20. Bond pattern 10 has a pattern length defined in terms of distance measured along central longitudinal axis 20, and a pattern width "W" represented by distance between first side edge 16 and second side edge 18 of bond pattern 10. Correspondingly, the overall area of bond pattern 10 is defined as the area which participates in absorbing and dissipating, by operation of bond pattern 10, stresses received into the bond pattern from external sources, the bond pattern area generally being defined within the confines of side edges 16 and 18.

In product implementations of the invention, the bond pattern reflects application of force which urges first and second thin-section e.g. sheet material elements toward each other in face-to-face relationship to form, as repeating bond segments, an array of separate, distinct, and spaced elongate bond elements in a repeating arrangement affixing the first and second thin-section elements to each other. Ones of the bond elements extend width-wise across the bond pattern, from loci proximate the side edges up to at least about the longitudinal axis, at angles "α" of between about 10 degrees and about 65 degrees, preferably about 15 degrees to about 50 degrees, with respect to the longitudinal axis. Most preferred angles are about 25 degrees to about 40 degrees The angles illustrated in the drawings represent about 30 degrees from the longitudinal axis.

While legs 26 are shown in the drawings as being straight, the legs can be curved in some embodiments. In such case, the respective angles "α" vary along the lengths of such legs in accord with the respective curvatures of the legs.

A bond width is defined by an end-to-end length corresponding to bond elements arrayed across the width of the pattern perpendicular to the longitudinal axis, including spaces between respective ones of the bond elements, and spaces between bond elements and side edges 16, 18. A bond width can be measured at any point along the length of the bond pattern, and such bond width extends along the pattern width. The bond width thus corresponds to the pattern width "W" at a given locus along the length of the bond pattern.

Bond element contact lengths at respective bond elements are correspondingly defined along the bond width. The additive combination of the bond element contact lengths along a respective bond width defines the composite contact length along the respective bond width. The composite contact length, taken at equally spaced intervals along a length of the bond pattern, defines an average composite contact length. The composite contact length at a given point along the length of the pattern varies from the average composite contact length by no more than about 13 percent, preferably by no more than about 10 percent, and more preferably by no more than about 8 percent.

In the illustrated embodiments, opposing pattern combinations 22 and 24 are substantially the same and are employed as off-set mirror images of each other. Thus, pattern combinations 22, 24 are positioned along the length of the pattern such that the opposing pattern combinations are asymmetric with respect to each other by expression of such offset. While the opposing patterns are asymmetric with respect to each other, both first opposing pattern combination 22 and second opposing pattern combination 24 are internally symmetric, as well as expressing repeating segments thereof along the length of bond pattern 10.

Bond pattern 10 is defined by a plurality of bond elements. In preferred embodiments, bond elements proximate side edges 16, 18 are spaced farther apart from each other than bond elements which are disposed more away from the side edges, thus creating a pattern density which is less dense at the side edges of the pattern than away from the side edges.

Bond pattern 10 preferably comprises regularly repeating bond segments, each repeating bond segment comprising a defined set of bond elements spaced according to a generally fixed segment pattern. A plurality of bond elements establishing repeated element combinations defines such bond segment, although not all bond elements need be defined in bond segments. Therefore, a similar bond pattern using one or more orphan bond elements which orphan elements do not repeat regularly, or which elements are so far outside the rest of the bond pattern that such bond elements do not cooperatively participate with the other bond elements in absorbing and dissipating, by operation of the bond pattern, stresses received into the bond pattern, is within the scope of the present invention.

The illustrated bond pattern comprises, as a first sub-array of the bond elements, longitudinally-oriented separate, distinct, and spaced stress receptor elements 12 disposed at or near, namely proximate, first side edge 16 and second side edge 18. Receptor elements 12 are typically evenly spaced along the length of bond pattern 10.

Stress transfer and dissipation elements 14 define a second sub-array of longitudinally-oriented separate, distinct, and spaced bond pattern elements, typically evenly spaced along the length of bond pattern 10, inwardly of the side edges of the bond pattern and typically inwardly of stress receptor elements 12. Each respective transfer and dissipation element has a first end 28 and a second end 29, and legs 26 extending from the respective ends toward each other and outwardly of the longitudinal axis, and meeting at an outwardly-disposed joinder locus 27 of the legs 26 between stress receptor elements 12. Stress receptor elements 12 alternate along the length, and on opposing side edges, of the bond pattern. Stress transfer and dissipation elements 14 alternate on opposing-sides, and along the length, of bond pattern 10, generally between respective stress receptor elements. Stress transfer and dissipation elements 14 thereby provide the desired side-to-side balance to the bond element width of bond pattern 10.

In general, then, preferred bond patterns comprise regularly repeating bond segments, each repeating bond segment comprising at least one stress receptor element 12 and at least one stress transfer and dissipation element 14, the elements 12 and 14 being spaced according to a generally fixed segment pattern wherein each stress receptor element 12 is balanced by a transfer and dissipation element, or a stress termination element, or both, or other balancing element or elements, on the opposing side of longitudinal axis 20.

Figure 3A:
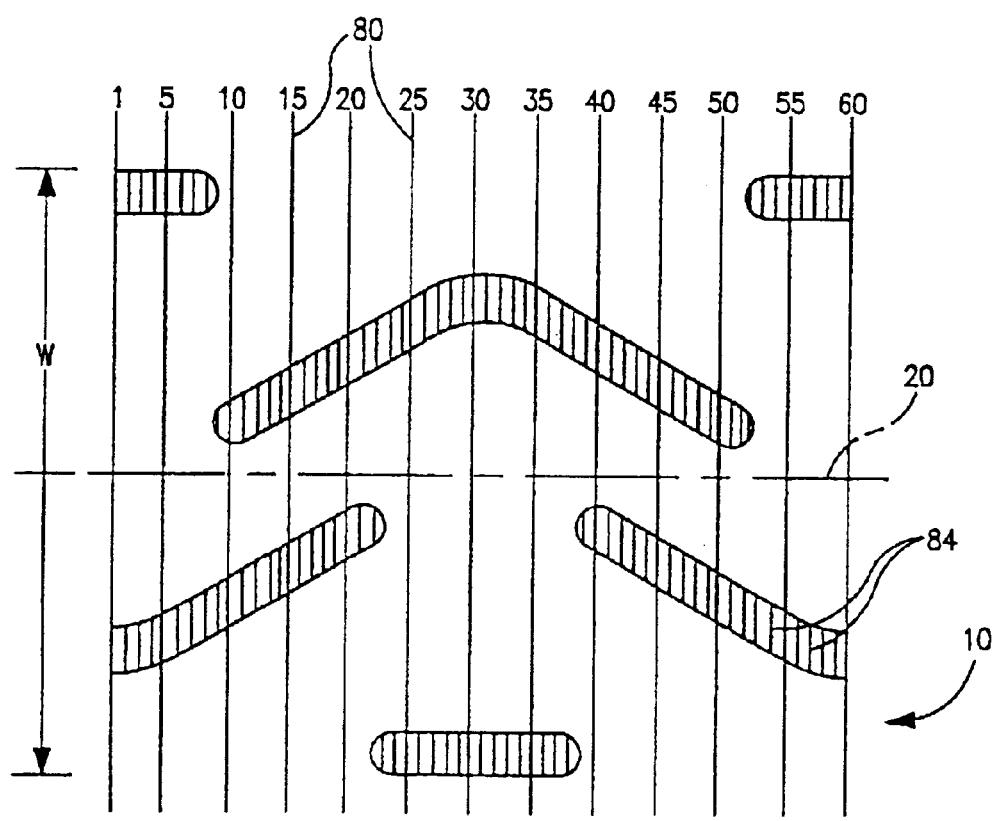
FIGS. 3A and 3B show enlarged representations of preferred relationships between respective elements of the bond patterns of FIGS. 1A and 1C, respectively.

In e.g. the embodiments illustrated in FIGS. 1A and/or 1B, an imaginary line 80, shown in FIG. 3A, along a given bond width at a given locus along the length of the bond pattern traverses a stress receptor element 12 on a first side of longitudinal axis 20 and a respective leg 26 of the corresponding transfer and dissipation element 14 on the opposing side of the axis. The distance between distal ends of the most remote ones of the bond elements along a respective imaginary line spanning the width of the bond pattern, so defined and illustrated in FIG. 3A, represents at least about 70 percent, up to 100 percent, of the width of the bond pattern, more preferably, at least about 75 percent up to about 90 percent, of the width of the bond pattern, and even more preferably at least about 80 percent up to about 85 percent, of the width of the bond pattern.

The distance between the ends of the composite contact length is illustrated as less than 100 percent of the width of the bond pattern, wherein the transfer and dissipation elements are located inwardly of side edges 16, 18. In some embodiments, the outer portions 82 of the transfer and dissipation elements can be disposed at side edges 16, 18, whereby the composite contact length can be as great as 100 percent of the width of the bond pattern at the given locus along the length of the web.

Thus, outwardly-disposed portions of respective legs 26 of the transfer and dissipation elements provide balancing support on opposing sides of the longitudinal axis balancing e.g. respective stress receptor elements 12 during formation of the bond pattern 10.

Because transfer and dissipation elements 14 extend both directions along the length of the bond pattern, elements 14 can transfer, to the interior of the bond pattern, stresses coming from either direction along the length of the bond pattern. Similarly, angles "α" of the transfer and dissipation elements 14 tend to promote the transfer of stresses to the interior of the bond pattern, and are effective to transfer stresses entering the bond pattern from any direction inwardly from the side edges and toward the interior of the bond pattern. Additionally, because of the similarity of the opposing pattern combinations located on opposing sides of central longitudinal axis 20, the bond pattern effectively balances nip force exerted on one side of the pattern with a balancing nip force on the opposing side of the bond pattern, while the bonds are being formed.

In an embodiment illustrated by FIG. 1B, and starting with the structure of FIG. 1A, portions of the transfer and dissipation elements where the legs join at 27 in FIG. 1A have been excised and moved to locations at or near central longitudinal axis 20 and on the same side of the pattern as the respective donor transfer and dissipation element, thus to provide respective stress termination elements 13. Stress termination elements 13 tend to coordinate degeneration, dissipation, and preferably termination, of stresses transferred into the interior portion of the bond pattern adjacent axis 20.

The resilience of materials known for use in e.g. the body side liner or the outer cover of absorbent articles, in combination with controlled pattern density, enables the bond pattern to direct inwardly toward the longitudinal axis a wide variety of forces imposed on the bond pattern from any direction along the length or width of the bond pattern. By directing, transferring, and distributing stresses toward the interior of the bond pattern, the invention relieves the side edges of the bond pattern from bearing a corresponding portion of the stress which is typically borne by side edge portions of the bond pattern. Thus, the stress born by the respective side edge when a given force is imposed on the bond pattern, is less for bond patterns of the invention than for a conventional bond pattern having a symmetrically arrayed square pattern of lines and rows of circular bond elements. Accordingly, bond patterns of the invention can tolerate more overall stress than such conventional bond patterns. Thus, not only does the bond pattern reduce the straight-line, perforation-like failure tendency of conventional linearly-arranged bond patterns, but the invention is correspondingly capable of tolerating and distributing greater levels of stress than a conventional bonding pattern.

Bond pattern 10 can be used to unite sheets of material along the entirety of the length of the material, or as in the case of the examples cited, along a portion of the length or width of a personal care absorbent article. Bond pattern 10 can also be used to unite intermittent portions of respective work pieces in a particular configuration e.g. defined in terms of length and/or width. Bond pattern 10 can further be used to unite portions of work pieces according to more than one configuration. Bond pattern 10 can yet further be used to unite materials along a defined length of web material. In all such implementations, bond pattern 10 can be used to bond a relatively smaller element or work piece to a relatively larger element or work piece. Examples of use of the bond pattern in an absorbent article include, but are not limited to, bonding a fastening ear to the outer cover, bonding a leg flap to the outer cover or the body side liner, bonding containment flaps to the body side liner, and bonding a landing zone to the outer cover.

In yet another embodiment, bond pattern 10 comprises a pattern density defined generally by the spacing and number of bond elements within a defined portion of the pattern area, wherein bond elements proximate the side edges are spaced farther apart from each other than bond elements which are disposed more away from the side edges, thus creating a pattern density which is less dense at the side edges of the pattern than away from the side edges.

FIG. 1C shows a bond pattern 10 having a first side edge 16 and a second side edge 18. A central longitudinal axis 20 divides the bond pattern 10 into a first pattern combination 22 and a second opposing pattern combination 24. Bond pattern 10 has a pattern length defined generally as the distance by which the pattern extends along the central longitudinal axis 20, and a pattern width "W" represented by the distance between first side edge 16 and second side edge 18. Correspondingly, the overall area of the bond pattern is defined as the area which participates in absorbing and dissipating, by operation of the bond pattern, stresses received into the bond pattern.

Figure 3B:
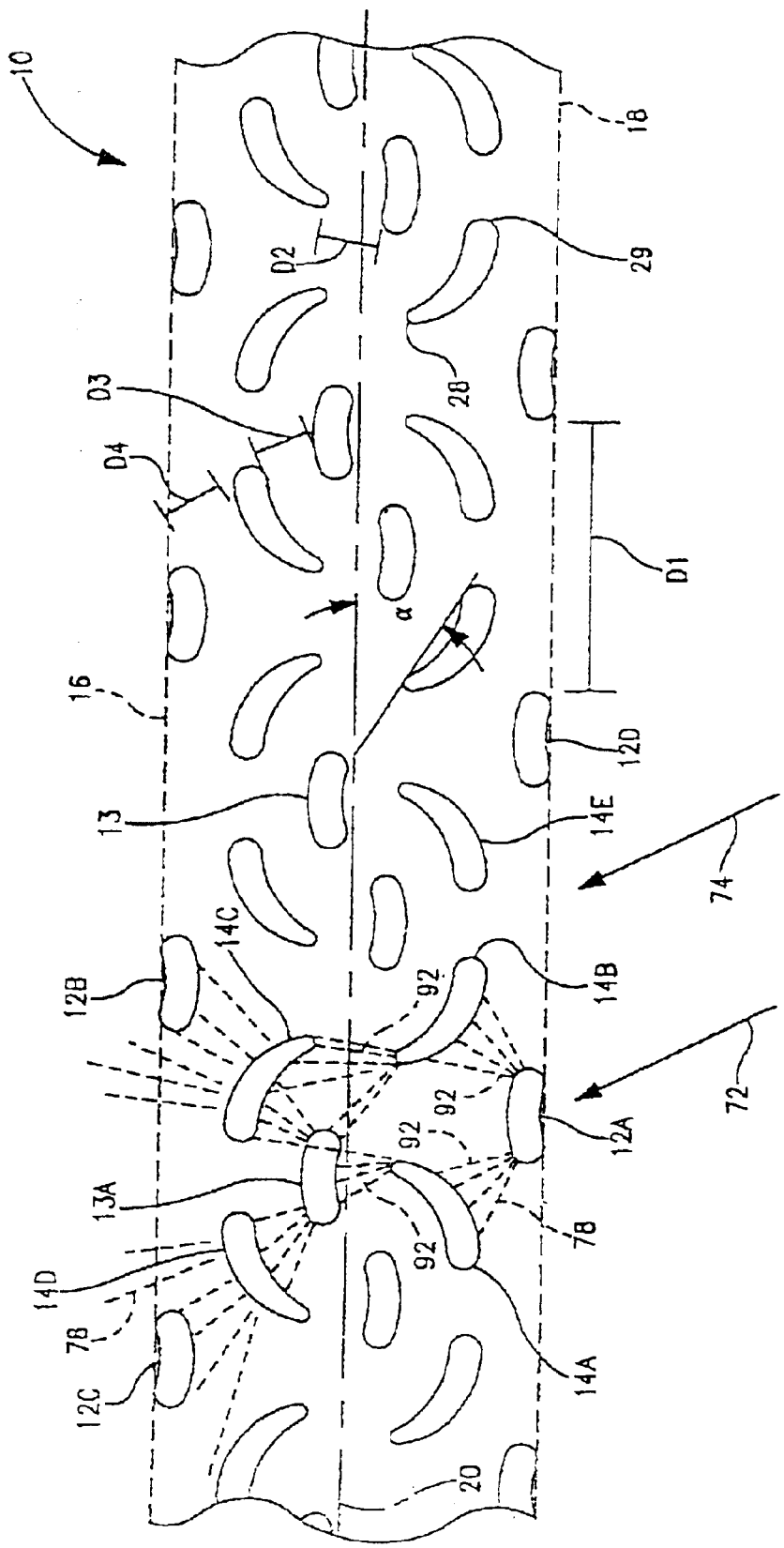

The embodiment of FIGS. 1C and 3B is more fully described in application Ser. No. 09/651,041, filed Aug. 30, 2000, of common assignment herewith, and herein incorporated by reference in its entirety.

The portion of bond pattern 10 of FIG. 1C which is located between central longitudinal axis 20 and first side edge 16 makes up a first pattern combination 22. Correspondingly, the portion of bond pattern 10 which is located between central longitudinal axis 20 and second side edge 18 makes up a second opposing pattern combination 24. In the embodiment of FIG. 1C, first opposing pattern combination 22 and second opposing pattern combination 24 represent substantially the same arrangement of bond elements and bond element relationships and are employed as off-set mirror images of each other The first and second opposing pattern combinations are positioned along the length of the pattern such that the opposing pattern combinations are asymmetric with respect to each other. While the opposing patterns are asymmetric with respect to each other, both pattern combination 22 and pattern combination 24 are internally symmetric, as well as being symmetric with respect to the length of bond pattern 10.

In one embodiment, bond pattern 10 comprises a pattern density defined generally by the number and spacing of bond elements within a defined portion of the pattern area, wherein bond elements proximate the side edges are spaced farther apart from each other than bond elements which are disposed more away from the side edges, thus creating a pattern density which is less dense at the side edges of the pattern than away from the side edges.

In the illustrated embodiment of FIG. 1C, each of the opposing pattern combinations comprises stress receptor elements 12 proximate the side edges of the bond pattern, transfer and dissipation elements 14 disposed inwardly of the stress receptor elements 12, and stress termination elements 16 disposed inwardly of transfer and dissipation elements 14. A plurality of such bond elements establishing repeated element combinations and spacial arrangements, along the length of the bond pattern, defines a repeat pattern.

Stress receptor elements 12 are shown in FIG. 1C, disposed proximate side edges 16 and 18, along the length of bond pattern 10 as a first sub-array of longitudinally-oriented separate, distinct, and spaced bond elements. Transfer and dissipation elements 14 are shown as a second sub-array of longitudinally-oriented separate, distinct, and spaced bond pattern elements spaced along the length of the bond pattern. The transfer and dissipation elements are disposed inwardly of the side edges of the bond pattern and generally inwardly of the stress receptor elements 12. A third sub-array of longitudinally-oriented separate, distinct, and spaced stress termination elements 13 is disposed generally inwardly of the transfer and dissipation elements 14 on opposing sides of, and oriented generally along, central longitudinal axis 20. In the illustrated embodiments, combinations of one stress receptor element 12 and two stress transfer and dissipation elements 14 alternate with each other along the length of the bond pattern on both sides of the bond pattern, and thereby provide a side-to-side walking advance of element groupings along the length of the bond pattern. Bond pattern combinations 22 and 24 are thus longitudinally asymmetric with respect to each other along the length of the bond pattern thereby to distribute the collective bond element widths relatively more evenly along the length of the bond pattern. Such distribution contributes to service life of the rolls used in a rotary bonding nip.

A stress transfer and dissipation element 14 is further defined as having a first end 28 and a second end 29. First end 28 of a transfer and dissipation element 14 is disposed at an interior portion of the bond pattern relative to the second end 29. The second end 29 of a transfer and dissipation element 14 is located outwardly in the bond pattern adjacent a respective side edge of the bond pattern between and inwardly of a respective one of the stress receptor elements 12. Second ends 29 of transfer and dissipation elements 14 are also distinguished from first ends 28 in that the second end 29 of a respective element 14 has a greater radius of curvature in plan view than first end 28 of the same element 14.

The several bond elements preferably occupy from about 10 percent to about 40 percent of the overall bond area of the bond pattern. In a more preferable application of bond pattern 10, the bond elements occupy from about 12 percent to about 30 percent of the overall bond area of the bond pattern. In an even more preferable application of bond pattern 10, the bond elements occupy from about 15 percent to about 25 percent of the overall bond area of the bond pattern. The specific preferred fraction varies from pattern to pattern, from process to process, and considering the material being bonded. If the bond element fraction is too low, the elements are unable to cooperatively support each other whereby the stress may not be adequately attenuated in the bond pattern and whereby a lack of minimum bond element density may result in layers of a bonded composite disassociating with one another. If the element fraction is too high, areas of the web between bond elements are not sufficiently extensive to enable unbonded areas of the web material, in the bond pattern area, to effectively distribute the stresses among adjacent bond elements, or to dissipate the stresses internally within e.g. unbonded portions of the bond pattern.

In some embodiments of the present invention, bond pattern 10 can be used to unite sheets of material along the entirety of the length of the material, or in the case of the examples illustrated herein, along the entirety of the length or width of an absorbent article.

In another family of embodiments of the present invention, bond pattern 10 can be used to unite intermittent segments of a defined length of the e.g. absorbent article.

In yet another family of embodiments of the present invention, bond pattern 10 can be used to unite variable-width segments of a length of the e.g. absorbent article.

In still another family of embodiments of the present invention, bond pattern 10 can be used to unite materials along a defined length of the materials being bonded. In all of the embodiments, bond pattern 10 can be used to bond smaller elements such as separate and distinct work pieces to a larger element such as a generally endless web.

Bond elements 12, 13, 14 have been described in terms of bonds formed by employing ultrasonic energy, thermal energy, and the like, in combination with pressure at a nip Other methods of forming such separate, distinct, and discrete bonds will be known to those skilled in the bonding art.

In this invention, adherent material, such as chemical adhesive material, can be used in forming the bond pattern, in combination with such bond elements. Such adherent material is preferably employed within the bond pattern as defined by the bond elements 12, 13, 14, and may extend outwardly or inwardly from the width of the bond pattern as defined by the bond elements. Such adherent material can be applied to one or both of the thin-section materials which are being bonded to each other. The methods which can be used for applying such adherent material to the thin-section elements are as varied as the methods conventionally known for applying adherent compositions to materials to be bonded to each other. Thus, typical methods of applying the adherent material include spraying from nozzles, coating from a coating roll, transfer roll coating, dip applications, wire rod spreaders, and the like.

The adhesives contemplated as being most commonly used in this invention are liquid adhesives, or are activated such as by melting prior to-being applied to the thin-section materials being bonded to each other, thus to temporarily become liquid for purposes of being applied to the materials being bonded; and after such application, such adherent material may then revert to a solid or deformable plastic state.

After the fluid adhesive is applied to one or both of the thin-section sheet materials, the sheet materials are brought together typically with pressure, such as in a nip, to develop bonding contact which bonds the sheet materials to each other through the adhesive. Such nip, if shown, would be between adhesive applicator 70 and nip 60 in FIG. 6. The thus adhesively-bonded sheet materials then pass through nip 60 where bond elements 12, 13, 14 ane the like are developed.

Given that the adhesive is typically liquid, or at least flowable, when being applied to the thin-section sheet material, the flowable/fluid adhesive is mobile, namely is susceptible to being moved about by forces exerted on such adhesive, while in the liquid, flowable, fluid state. A result of such fluidity of the adhesive, when being used in such bonding operation, is that the force used to develop the adhesive bonds, as well as the force used to develop the separate bond elements, e.g. 12, 13, 14, correspondingly develop fluid pressure on the liquid adhesive as the adhesive passes through a corresponding nip. Such fluid pressure e.g. at nip 60 or an earlier nip causes flow of such fluid adhesive to areas of lower fluid pressure. Such areas of lower fluid pressure exist transversely as well as longitudinally along the length of the bond pattern, from nip 60. While longitudinal movement of the adhesive relieves the pressure temporarily, the moved adhesive re-enters the respective nip as the substrate continues to advance through the nip. Accordingly, permanent relief of the fluid pressure on particular elements of the fluid adhesive is achieved through movement of the adhesive transversely across the width of the nip/bond pattern, whereby the moved adhesive traverses through the nip and out the downstream side of the nip. Such transverse movement of the adhesive can result in an expansion of width of that portion of the bond pattern which is defined in terms of adherent material such that such movement of adhesive effectively defines one or both outer edges of the adherent material portion of the bond pattern.

The overall result, of using a bond pattern of bonding elements in combination with the adherent material around some or all of the bonding elements, is a synergy of cooperative distribution, dissipation, and termination of stresses imposed on the bond pattern. The pattern of adherent material in the combination especially promotes use of corresponding areas of both layers for stress distribution, for energy absorption, and for discouraging fracture of sheet material at the bond pattern.

Because of such mobility of the adhesive, it is important that the width of the pattern of adhesive which is laid down, and the density of adhesive material to be laid down, in combination with the amount of pressure applied at the bonding nip, the density and spacing of bond elements created at the nip, and the uniformity of pressure applied to the elements being bonded at the nip, all be considered in arriving at target width and target location for applying the adhesive.

The adhesive passes through the nip after being applied to the material to be bonded (e g, a substrate/web), and while the adhesive is still mobile. Accordingly, the pressure exerted at the nip causes the adhesive to move especially transversely in the substrate or web thereby potentially changing the width of the adhesive pattern. Once the adhesive reverts to an immobile form, e.g. downstream of the bonding nip, the resulting width is stabilized. Such stabilized width is represented in FIGS. 2A, 2B, 2C, and 2D by the dashed lines at opposing sides of the respective FIGURES.

Referring first to FIG. 2A, first side edge 16 of adhesive pattern 11 is generally coincident with the outer extremities of pattern 10 of bond elements. FIG. 2A illustrates at first side edge 16 a more wavy line indicating the uneven-ness which may attend transverse movement of adhesive material as a result of the pressure at the nip. The second side edge 18 in FIG. 2A is substantially straight, more representative of a side edge not so affected by movement of the adhesive in the bonding nip.

FIG. 2B illustrates the embodiments wherein adhesive pattern 11, and thus side edges 16, 18 of the bond pattern, can extend outwardly on both sides of bond pattern 10 from that potion of the bond pattern represented by the bond elements.

Figure 2C:
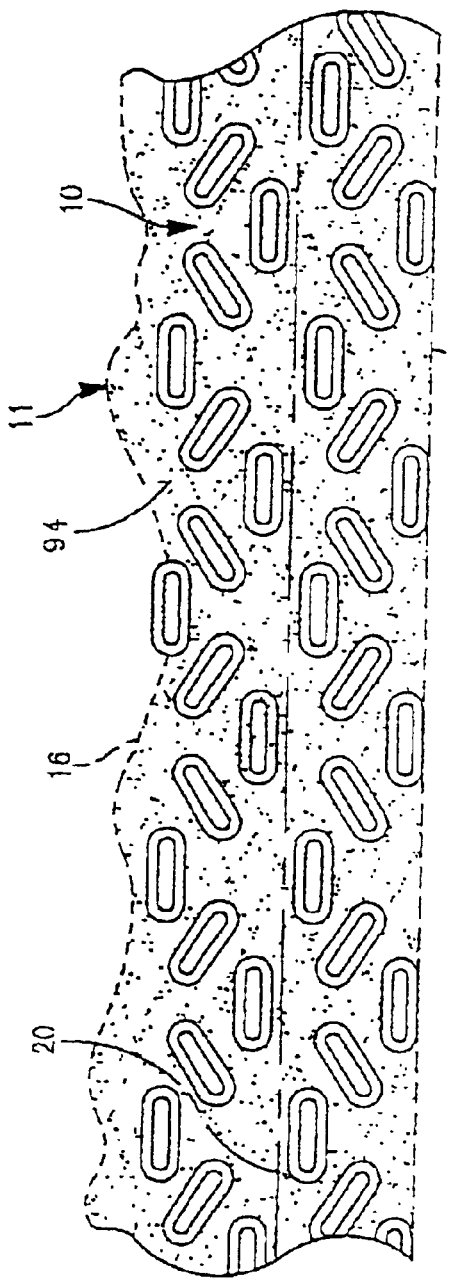

FIG. 2C illustrates preferred embodiments wherein, on a lower side of bond pattern 10, adhesive pattern 11 is coincident with second side edge 18 of bond pattern 10, as defined by the bond elements, and on the opposing side of bond pattern 10, the adhesive extends somewhat outwardly from the bond elements to form a wavy side edge 16 outside that portion of the width of the bond pattern which is represented by the bond elements.

Having the adhesive extend outwardly from that portion of the width of the bond pattern which is represented by the bond elements provides plural benefits. First, the adhesive provides an advance area first line of stress relief, such that the adhesive receives and distributes the stress to both thin-section elements before the stress reaches any of the bond elements.

Second, where the adhesive is generally consistently distributed throughout the general area of its coverage, the adhesive provides for a continuum of stress distribution to both thin-section web elements throughout the full bonded area of the substrates or sheet material, affected by the stress, as opposed to only the discrete areas defined by the bond elements, or only a single one of the sheet material elements, whereby uniformity of stress distribution in the thin-section elements is enhanced, which typically results in enhanced dissipation and termination of stresses.

Figure 2D:
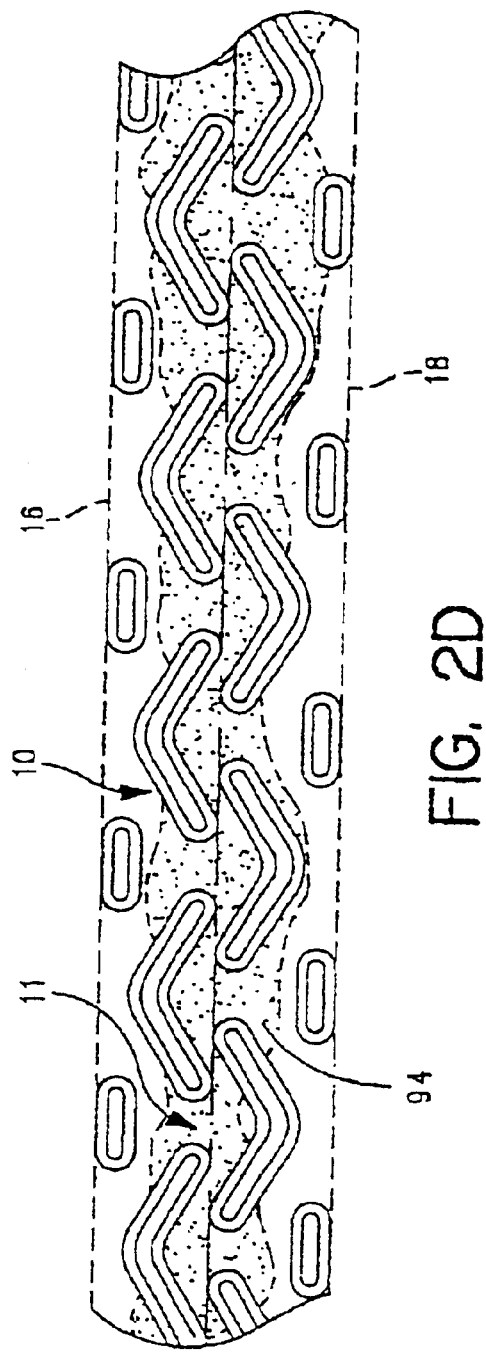

FIG. 2D illustrates embodiments wherein the outer edges of adhesive pattern 11 are disposed inwardly from side edges 16, 18 as defined by the bond elements. Such inward disposition of the adhesive at the interior of a bond pattern which is configured to transfer the stresses into the interior of the bond pattern focuses the strength of the adhesive material in the bond pattern at locations of the bond pattern where the adhesive material can provide the greatest effectiveness. Namely, the strength of the adhesive is focused on the areas of greatest need for dissipation of stress, while leaving to the bond elements the tasks of receiving and directing the stresses toward the interior of the bond pattern.

In general, the benefit of the adhesive pattern inside the side edges where the side edges are defined by the bond elements, is to improve distribution of the stresses throughout the areas of the thin-section elements which are susceptible to being affected by the bond pattern. In that regard, the bond pattern is defined as the composite of the bond elements, and the adherent material, to the extend the adherent material works in combination with the bond elements in controlling stress reception, distribution, transfer, dissipation, and termination.

Where the adhesive pattern at least reaches, from inwardly of the side edges as defined by the bond elements, to the side edges, adhesive between e.g. stress receptor elements tends to initiate the stress reception response, between the stress receptor elements, at the dashed line representing the edge of the adhesive material. Without the presence of the adhesive material, initiation of response to stress at such location requires traverse of the stress either to an adjacent but displaced stress receptor element or to an adjacent but displaced transfer and dissipation element. In either case of absence of adhesive material at edge 16 or 18, response to the stress is transferred from the local area where the stress crosses the side edge of the bond pattern as defined by the straight line connecting the stress receptor elements, whereby the stress reception response is somewhat less effective.

Typical adhesive patterns of the invention generally at least direct a stress inwardly into the bond pattern. The adhesive patterns typically are continuous along at least a portion of the width of the bond pattern, and typically interact with the bond elements to the extent of sharing distribution and dissipation of the stresses imposed on the bond elements. Typically, the adhesive pattern extends to some degree on both sides of longitudinal axis 20, and is typically generally centered along axis 20, as illustrated in FIGS. 2A, 2B, 2C, 2D.

Within the width defined by the adherent material pattern, the adherent material is typically continuous along such width, and such width is typically constant, or generally constant within manufacturing capability to maintain such consistent width. The width variations shown in the drawings are exaggerations for illustration purposes of the variations which are typically encountered in commercial implementations. However, such variations are not generally preferred, and engineering work may be employed to attenuate such variations.

While the side edges can be defined functionally by those areas of the respective thin-section elements which participate in absorbing and dissipating, by operation of the bond pattern, stresses received into the bond pattern from external sources, the side edges can also be defined structurally. Namely, peripheral portions of those areas of the respective thin-section elements which participate in absorbing and dissipating the stress can constitute the side edges of the pattern. The peripheral portions of such areas at particular loci can be defined as those bonded areas which are furthest disposed from the central longitudinal axis and are disposed outwardly of ones of the bond elements, e.g. the stress receptor elements at the particular loci.

FIG. 3A shows an enlarged view of the bond pattern illustrated in FIG. 1A. FIG. 3A includes imaginary connection lines 80 spaced evenly along the length of bond pattern 10, to help illustrate the relationships between the respective bond elements and the cooperative effect of such spacial relationships as the positioning of the respective bond elements works to increase the wear life of both lower-disposed e.g. anvil roll 62B (FIG. 6) and upper-disposed roll 62A.

FIG. 3A represents a single repetition of the bond pattern illustrated in multiple repetitions in FIG. 1A. In FIG. 3A, the several bond elements are shown divided by equally spaced imaginary increment lines 84 which extend perpendicular to longitudinal axis 20, and parallel to lines 80. In FIG. 3A, each fifth line 84 is aligned with one of the lines 80. Thus, each fifth line 84 represents incremental portions of the length of a corresponding one of imaginary lines 80.

Lines 80 are used as convenient tools for indexing and evaluating the significance of lines 84. The spacing between respective lines 84, and the frequency of lines 80, can be selected as convenient for the user's analysis. In the illustrated embodiment, the distances between adjacent imaginary increment lines 84 are approximately 0.008 inch. Such distances are preferably uniform along the length of the pattern being evaluated. The length of the imaginary increment lines 84 generally represents at least the width "W" of the bond pattern. Each such distance defines one of the five increments used in defining a corresponding imaginary line 80. The illustrated bond pattern is designed to keep the composite contact length, which is indicative of the sum of the lengths of respective line segments of any one line 84 defined by each respective bond element crossed by any one line 84, including all sections thereof, within 0.010 inch of the average composite contact length. The illustrated pattern is also designed so that those projections or lands which are collective in forming the nip have combined widths which define the composite contact length, and which are relatively consistent as measured along successive adjacent lines 84, over the full length of the segment, and wherein successive segments are both internally consistent within themselves, and are consistent with respect to each other.

One of the primary benefits of embodiments of the invention illustrated in FIGS. 1A and 1B is attenuation of power feedback spikes in ultrasonic bonding embodiments of the invention. Such feedback spikes occur as a result of characteristics of conventional bond patterns on e.g. a rotary anvil. Power tends to be a function of rotation of the rotary anvil, e.g. 62B, combined with forces emitted from one or both of the horn and anvil. The emitted forces can be any of forces selected from the group consisting of pressure, ultrasonic energy, and thermal energy as applied over time. Increases and decreases in power distribution across the width of a bond pattern can be defined by variations in composite contact lengths as compared to the average composite contact length for a given bond pattern for at least a complete circumferential rotation of an anvil.

Conventional bond patterns tend to demonstrate a wide variation in composite contact lengths as compared to respective average composite contact lengths. A given proportional variation in composite contact lengths causes the same proportional variation in power distribution for a conventional bond pattern. The variation is typically attendant e.g. bond patterns being created in a straight, linear-type arrangement of circular bonding elements. Embodiments of FIGS. 1A, 1B of the invention preferably demonstrate a variation in composite contact length of no more than about 13% from the average composite contact length as the respective anvil makes a complete rotation. The consistency in power distribution of the such embodiments demonstrated by the lack of variance from the average composite contact length can also be indicative of consistency of resistance between the horn and anvil, as contact area in the nip is a function of the respective composite contact lengths. Thus, reduction in variation of respective composite contact lengths from the average composite contact length, as in some embodiments of the invention, results in a steady power distribution across the width of the bond pattern, and attenuation or avoidance of power spike feedback.

In addition, the side-to-side balance of the pattern and the consistency of the composite contact length provide two further benefits. First, bending stress is attenuated on shafts supporting rolls 62A, 62B. Second, where roll 62B is the patterned roll, side-to-side surface wear on especially roll 62A is relatively more uniform, providing longer roll life than patterns not exhibiting such consistency of composite contact length.

Referring to FIG. 3A, the composite contact length is defined as the sum of the line lengths along the widths of the bond elements traversed by a given imaginary increment line 84 between side edges 16 and 18. In the illustrated embodiment, imaginary increment lines are typically about 0.030 inch long on each respective bond element, and the overall pattern width "W" is about 0.38 inch. In such illustrated environment, variation in the composite contact length should be within 0.010 inch of the average composite contact length of such segments.

Figure 8:
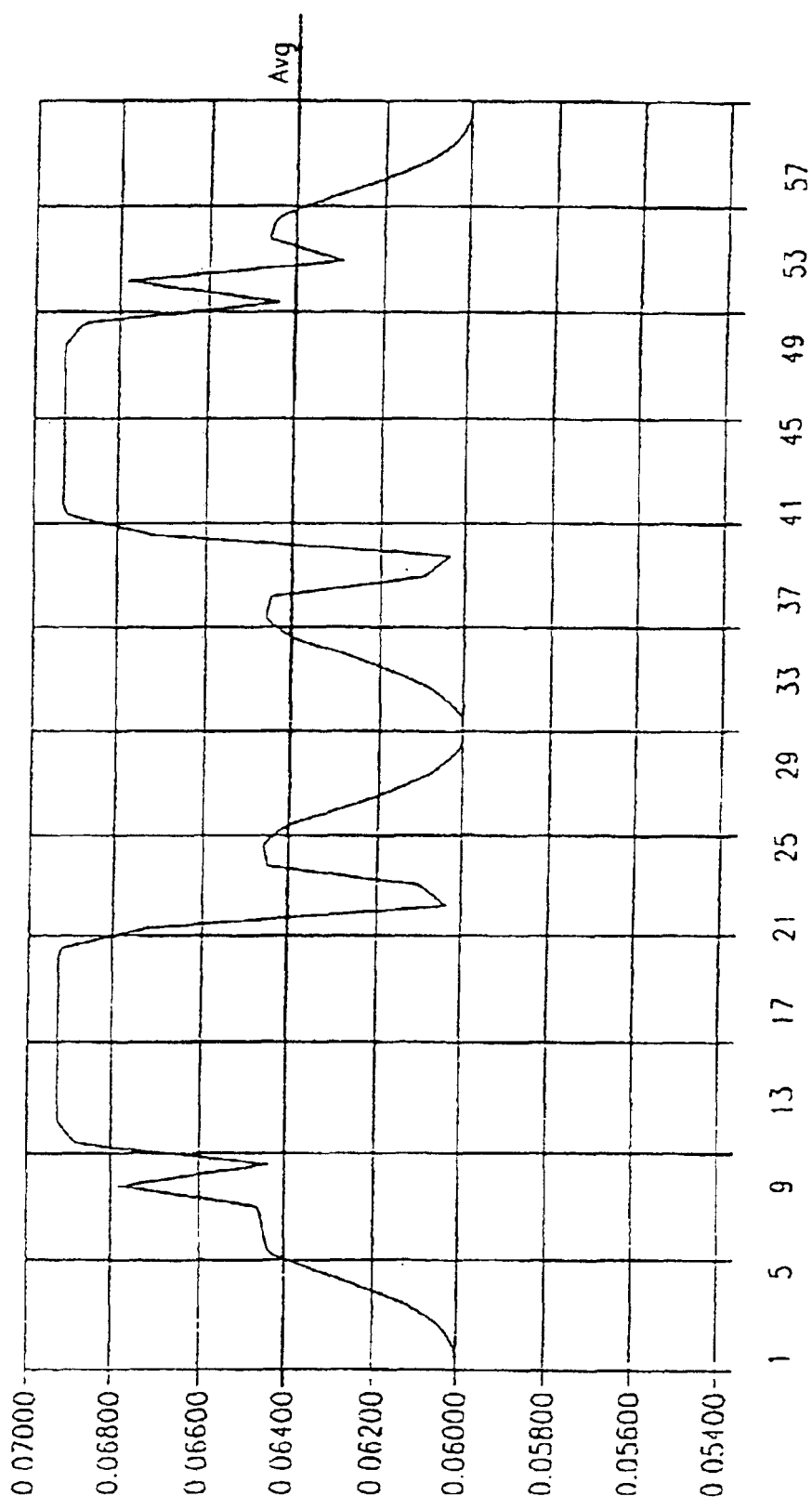
FIG. 8 shows a graph of the composite contact lengths of respective spaced locations illustrated in the table of FIG. 7.

Referring to FIG. 3A, an important value in bond patterns of the invention is that, during formation of the bond elements in the webs and/or work pieces, the loci of bonding contact in the nip can be consistently represented by bond elements on both sides of longitudinal axis 20. For example, at any time during which a stress receptor element 12 is receiving pressure in the nip, a transfer and dissipation element 14 on the opposing side of axis 20 is also receiving pressure in the nip. Thus, any force on a supporting roll shaft arising from receptor element 12 is countered by a second force, on the working face of the roll, arising from the opposing transfer and dissipation element 14, and tending to balance the first force. FIGS. 7 and 8 illustrate such analyses for each of the 60 line combinations 84 represented in FIG. 3A.

In addition to the reduction in shaft stress, such balanced pattern on the anvil roll provides for balanced wear across the width of the working surface of roll 62A. Such improved wear is especially valuable in an ultrasonic horn 62A which is used when the bonds are formed using an ultrasonic bonding process. Indeed, the improved surface wear benefits are more apparent where rolls 62A, 62B have different base diameters. In ultrasonic bonding processes, anvil roll 62B typically is designed to have a diameter different from that of the ultrasonic horn so as to not unacceptably attenuate resonance of the horn. Additionally, an anvil having a different diameter avoids wear associated with respective surface portions of the horn repeatedly interacting with corresponding surface portions of the anvil.

To that end, the pattern of some preferred embodiments can be suitably balanced, side to side, where the distance between distal ends of the most remote ones of the bond elements along a respective imaginary line spanning the width of the bond pattern so defined represents a width at least 70 percent as great as the width "W" of the bond pattern at the respective segment. Preferred distance between distal ends is about 80 percent to 85 percent of width "W." The distance may be as great as 100 percent where e.g. bond elements 14 extend to the side edges of the bond pattern. However, some such embodiments may be subject to stress transfer along the length direction of the resultant bond, at the side edges of the bond pattern, whereby the design of such bond patterns must consider how stresses can be assuredly transferred from the receiving bond elements, e.g. stress receptor elements 12, toward the interior of the bond pattern, and away from the side edge, as taught herein.

Referring to FIG. 3B, a stress vector 72 received at receptor element 12A is transmitted from receptor element 12A at the loci of smallest radius on the side of the receptor element opposite the stress receiving side. Dashed lines 92 illustrate the paths along which the stress traverses, away from receptor element 12A to transfer and dissipation elements 14A, 14B. The received stresses are similarly transmitted to the opposing sides of elements 14A, 14B, and thence outwardly from the smallest radius portions to element 14C and termination element 13A, thence to elements 12B and 12C. The above paths of transmission of the force into and through the interior of the bond pattern are indicated as paths 92 in FIG. 3B. The indicated paths are merely illustrative, and not limiting, of the distribution of forces in bond patterns of the invention. However, such illustration is instructive that bond patterns of the invention, given the angles "α" and the spacing between receptor elements 12, actively direct stresses into the interior of the bond pattern wherein a plurality of bond elements simultaneously absorb portions of the stress such that no one or two bond elements at the side edge of the bond pattern bear the entire burden of the stressing force. In the example of force vector 72, the stress is illustrated as being borne primarily by four bond elements 14A, 14B, 14C, and 13A, three of which are larger in size than the receiving element 12A, and thus can theoretically tolerate greater amounts of stress than can receptor element 12A.

In summary, a bond pattern of the invention operates as a compilation of various and differing functioning bond elements of the bond pattern, along with the support of adhesive material between the bond elements. The side edges, and thus the unit area, of the bond pattern are defined generally by those areas of the respective thin-section elements being bonded which participate in absorbing and dissipating, by operation of the bond pattern, stresses received into the bond pattern.

As stress is applied to a bonded composite or absorbent article demonstrating a bond pattern of the invention illustrated in the drawings, stress is initially received at the side edge of the bond pattern by an edge bond element such as a stress receptor element 12 and substantial portions of the received stress are typically transferred to the next closest bond element, namely one or more of the transfer and dissipation elements. By designing the bond pattern so that the next closest bond element is located inwardly on the bond pattern, substantial portions of the stress are transferred inwardly of the bond pattern and away from the respective side edge, whereby the amount of stress dissipated, absorbed at the side edge is lessened by the amount of stress which is transferred inwardly into the bond pattern. By disposing elements 14 at angle "α" with the longitudinal axis, the stress travels inwardly not only in being transferred from bond element to bond element, but also in traveling along the length of bond elements 14 toward the inner ends of such elements.

To the extent the resultant stress is reduced at the side edge, by transfer inwardly from the side edge, the side edge may have unused stress-accepting capacity, whereby the bond patterns of the invention have increased stress-bearing capacity compared to otherwise similar and conventional bond patterns.

The increased stress-bearing capacity of bond patterns of the invention is attributable to the cooperative relationships among the respective bond elements, as well as the structures and orientations of the respective bond elements. Stress receptor elements 12 initially receive stresses and relay the stresses inwardly to the next closest bond element in the pattern, for example an element 14. Stress transfer and dissipation elements 14 direct stresses inwardly further into the interior portion of the bond pattern, and the stresses are dissipated in the interior portion of the bond pattern.

Thus, assuming the tear strength of the material being bonded is not exceeded, bond patterns of this invention provide increased tear-resistance in a bonded composite, e.g. a bonded absorbent article, as compared to conventional bond patterns, by providing greater distances between adjacent bond locations for the pattern periphery, where the force-generated stress on the bond pattern is the highest. At the same time, the pattern is also conducive to maintaining the structural integrity of a rotary horn and anvil system by providing a relatively constant surface area contact, and side-to-side contact balance, between the horn and anvil.

While this invention has been described in terms of elongate bond elements, a limited number of circular bond elements can be used in the bond pattern so long as the number and placement of such circular bond elements are consistent with the principles taught herein for directing stress inwardly away from the side edges of the bond pattern.

Bond patterns of the invention typically comprise bond density of about 15 percent to about 50 percent, more preferably about 20 percent to about 40 percent. As used herein, "bond density" refers to the fraction of the bond area which is occupied by bond elements, e.g. stress receptor elements 12, stress transfer and dissipation elements 14, and/or stress termination elements 13. Such spacing of the bond elements from each other provides for distribution of stresses across unbonded portions of the bond pattern to a plurality of bond elements, albeit optionally through adhesively bonded portions of the thin-section sheet materials, thereby to enhance distribution of the stress over a relatively larger number of bond elements, as well as over a relatively larger area of the material being bonded. Such increased distribution of the stress operates to reduce the level of stress borne by a localized area of the bond pattern, thus reducing the maximum stress response intensity experienced by the bonded materials.

Figure 4A:
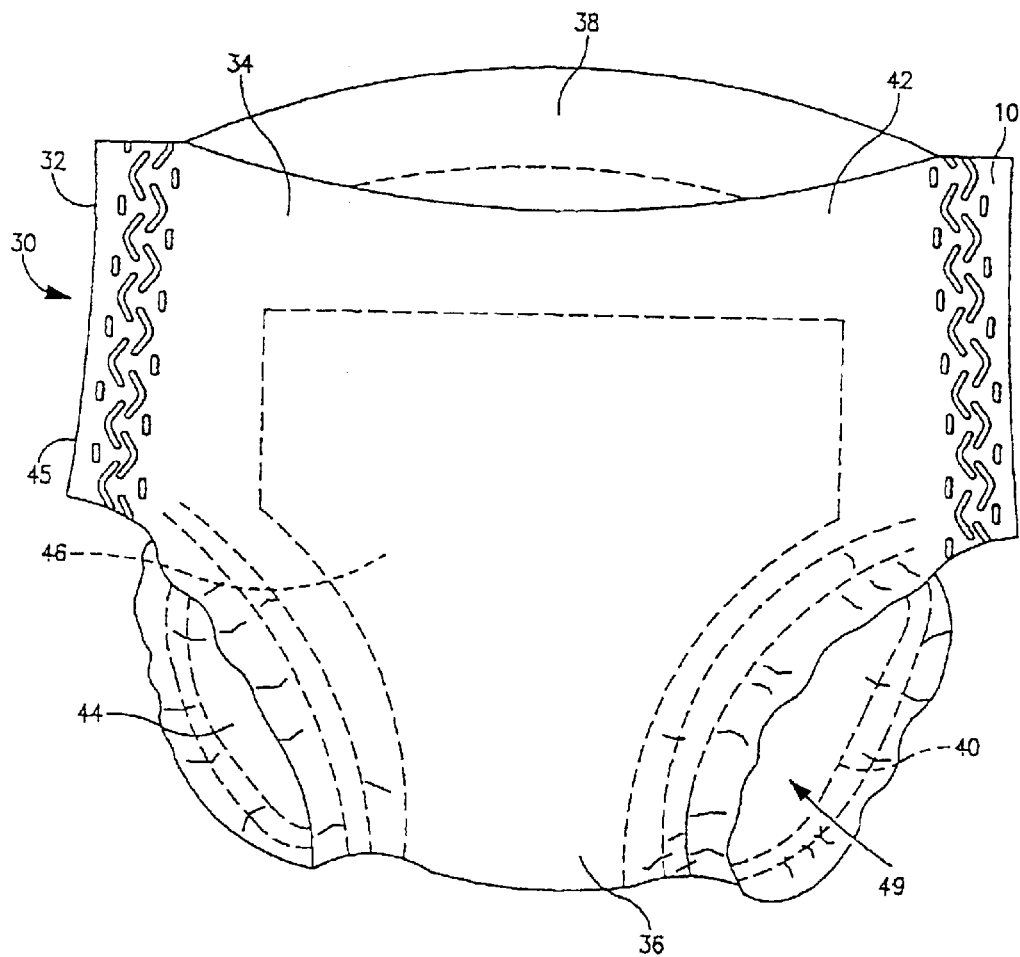
FIGS. 4A and 4B each show, as a representative absorbent article, a pair of training pants illustrating use of the bond patterns of FIGS. 1A and 1C, respectively, along the side seams.
Figure 4B:
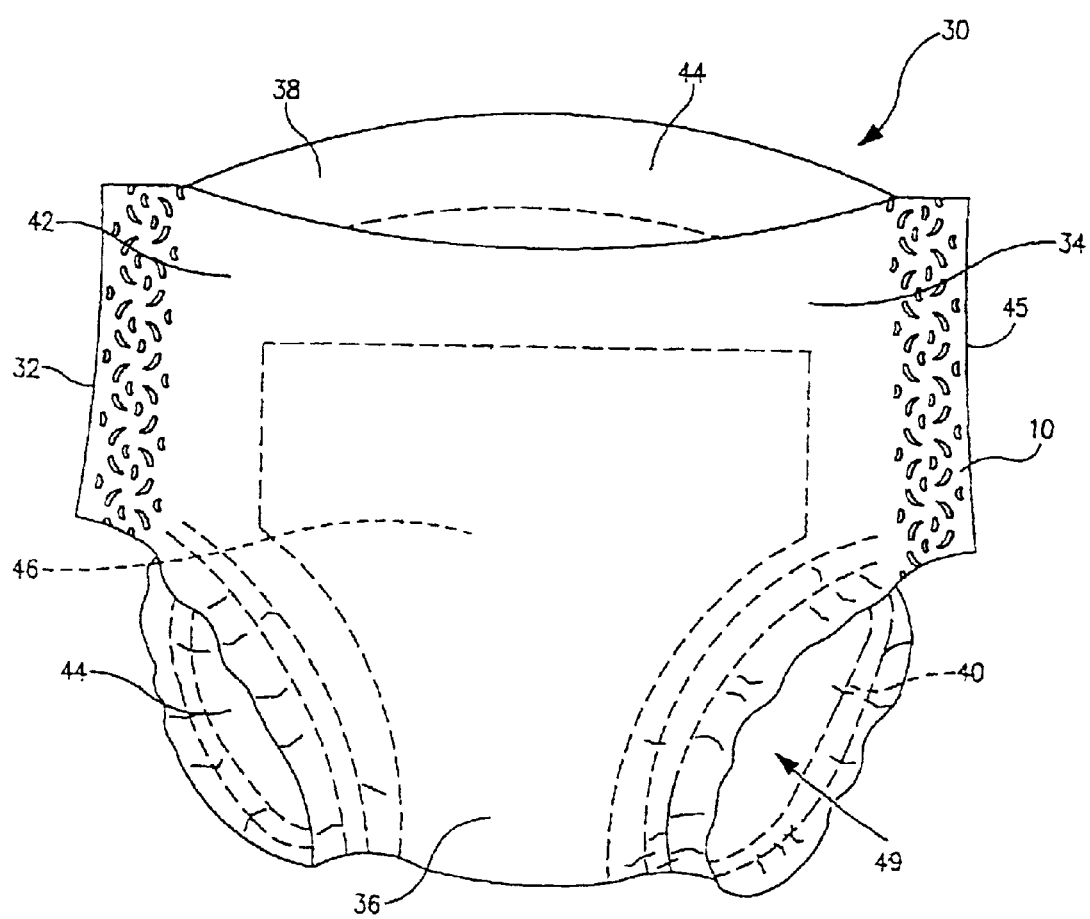

Referring to FIGS. 4A and 4B, an exemplary absorbent article, namely a pair of training pants 30, illustrates the use of bond pattern 10 of FIGS. 1A and 1C, respectively. In FIGS. 4A and 4B, the training pants have a front portion 34, a rear portion 38, and a crotch portion 36 which extends from front portion 34 to rear portion 38. The absorbent article of FIGS. 4A and 4B comprises a liquid-impermeable outer first thin-section element of sheet or web material as outer cover 42, a liquid-permeable body side second thin-section element of sheet or web material as body side liner 44, and a liquid-absorbent core 46 disposed between the outer cover and the body side liner. Side seams 32 employ the illustrated bond patterns 10 to join the front and rear portions at side edges 45. Leg elastics 40 extend along leg openings 49.

Various woven and nonwoven fabrics may be used in fabricating body side liner 44. For example, body side liner 44 can be fabricated using a perforated or reticulated film, or a meltblown or spunbonded web of polymeric material selected from the group consisting of polyolefins including polyethylenes and polypropylenes, polyesters, and polyamides, and mixtures, copolymers, and blends of such polymeric fibers. The body side liner can also comprise, alone or in combination, a carded and/or bonded web composed of natural and/or synthetic fibers. Body side liner 44 can also be composed of a substantially hydrophobic material wherein the hydrophobic material is treated with a surfactant or otherwise processed to impart a desired level of wettability and hydrophilicity.

Body side liner 44 can comprise, for example, a nonwoven, spunbonded, polypropylene fabric employing about 2.8–3.2 denier fibers formed into a web having a basis weight of about 22 grams per square meter and a density of about 0.06 grams per cubic centimeter. The fabric is then surface treated with about 0.3 weight percent of a suitable surfactant. Body side liner 44 can also be fabricated employing a fibrous web defining a multiplicity of randomly-spaced small openings extending from a major surface of the web into the interior of the web. The body side liner 44 can comprise material structure such as porous foams, reticulated foams, apertured polymeric films, polymeric fibers, and natural fibers. The body side liner can be defined in terms of length, width, and/or thickness by a multiplicity of components or layers which correspond with any of the materials disclosed herein, as well as others known in the art.

It is generally preferred that outer cover 42 of the absorbent article be formed from material which is substantially impermeable to liquids. A typical outer cover can be manufactured from a thin plastic film or other flexible liquid-impermeable material. For example, the outer cover can be formed from a film of polymeric material selected from the group consisting of polyolefins including polyethylenes and polypropylenes, polyesters, and polyamides, and mixtures, copolymers, and blends of such polymeric materials, the resulting outer cover having a thickness, for example, of from about 0.012 millimeter to about 0.051 millimeter. If outer cover 42 should have a more cloth-like feeling, the outer cover can comprise a polyethylene film laminated to a surface of a nonwoven web, such as a spunbonded web of polyolefin fibers.

For example, a polyethylene film having a thickness of about 0.015 millimeter can have thermally or otherwise laminated thereto a spunbonded web of polyolefin fibers having thicknesses of from 1.5 to 2.5 denier per filament, which nonwoven web has a basis weight of about 24 grams per square meter. Further, outer cover 42 can be formed of a woven or nonwoven fibrous web which has been totally or partially constructed or treated to impart a desired level of liquid impermeability to selected regions which are adjacent or proximate absorbent core 46. Still further, the outer first thin-section element 42 can optionally be composed of a micro-porous material which permits vapors to escape from absorbent core 46, through outer cover 42 and into the ambient environment, while preventing liquid exudates from passing through the outer cover.

One or both of the outer cover and the body side liner can comprise a fibrous web defining a multiplicity of randomly-spaced small openings extending from a major surface of the web into the interior of the web. Polymeric material selected from the group consisting of polyolefins including polyethylenes and polypropylenes, polyesters, and polyamides, and mixtures, copolymers, and blends of such polymeric materials can be used, in either film form, solid or reticulated, or in non-woven fiber forms, for one or both of body side liner 44 and outer cover 42. Also, included in definitions of the above polymeric materials are all routine, common, and normal additives known to those skilled in the art of polymeric materials, such as for example and without limitation, processing aids, chemical stabilizers, compatibilizers where more than one polymer is used, and fillers.

Absorbent core 46 suitably comprises a matrix of hydrophilic fibers, such as a web of cellulosic fluff, in combination with a high-absorbency material commonly known as superabsorbent material. Absorbent core 46 can comprise a mixture of superabsorbent hydrogel-forming particles and wood pulp fluff. In place of the wood pulp fluff, one can use synthetic polymeric e.g. meltblown fibers or a combination of synthetic fibers and natural fibers. The superabsorbent material can be substantially homogeneously mixed with the hydrophilic fibers or can be otherwise combined into absorbent core 46.

Absorbent core 46 can comprise a laminate of fibrous webs, optionally including an uncreped through-air dried (UCTAD) cellulosic material, in combination with superabsorbent material, or other suitable means of maintaining a superabsorbent material in a localized area.

Absorbent core 46 can have any of a number of shapes. For example, absorbent core 46 can be rectangular, I-shaped or T-shaped. It is generally preferred that absorbent core 46 be narrower in the crotch portion than in the rear portion or the front portion of the absorbent article to the extent the absorbent article includes a waist portion, which waist portion typically has a greater width than the width at the crotch portion.

The high-absorbency material in absorbent core 46 can be selected from natural, synthetic or modified natural polymers and materials. The high absorbency material can be inorganic material, such as silica gels, or organic compounds such as polymers, e.g. cross-linked polymers. "Superabsorbents," which are optionally cross-linked materials, as referred to herein, refers to any means for effectively rendering normally water-soluble materials substantially water insoluble but swellable, whereby absorbent properties are available but the swelled material is substantially immobile after absorbing water-based liquids. Such means can include, for example and without limitation, physical entanglement, crystalline domains, covalent bonds, ionic complexes and associations, hydrophilic associations such as hydrogen bonding, and hydrophobic associations or Van der Waals forces.

In embodiments of the invention indicative of an absorbent article as e.g. illustrated in FIGS. 4A and/or 4B, the width of the bond pattern between the first and second side edges of the bond pattern is preferably about 4 millimeters to about 20 millimeters, and more preferably about 5 millimeters to about 14 millimeters. In some contemplated embodiments of the invention, the width of the bond pattern may be up to about 4 inches.

The greater the width of the bond pattern, the more material can be included in the stress attenuation process, but the more material is used and, for a fixed number of bond elements, the greater the risk that the stress can pass through the bond pattern without being terminated. Thus, if the bond element-to-pattern area ratio is too low, the elements are unable to cooperatively support each other whereby stress may not be adequately attenuated in the bond pattern and whereby a lack of minimum bond element density may result in layers of a bonded composite disassociating with one another. Conversely, the less the width of the bond pattern, the less is the quantity of material used, but the greater the risk of not effectively spreading the stress away from the entry loci at the respective side edge and attenuating the stress. Thus, selection of a preferred specific width is a judgement to be made based on the technical features present in a given set of circumstances, including consideration of the principles of the invention.

Figure 5:
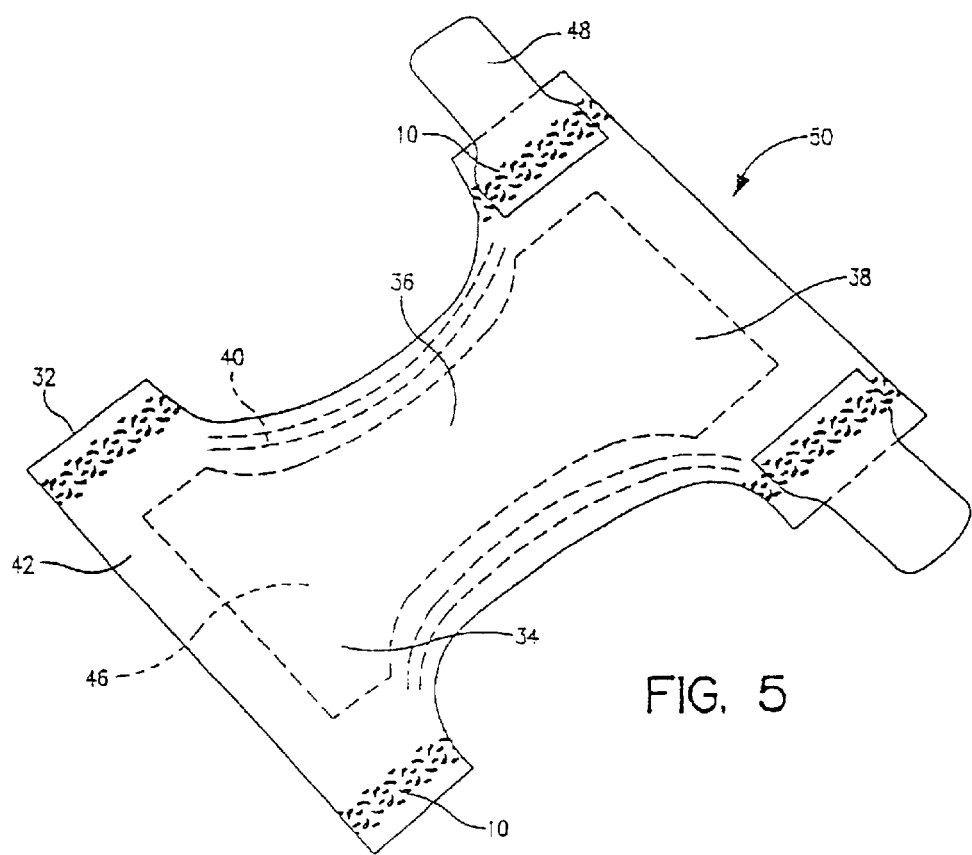
FIG. 5 shows, as another representative absorbent article, a diaper illustrating use of the bond pattern of FIG. 1C along the side seams as well as to adhere the ears to the outer cover.

FIG. 5 illustrates a diaper 50 of the invention utilizing the bond pattern of FIG. 1C. Diaper 50 has a front portion 34, a rear portion 38, and a crotch portion 36 which Joins the front portion 34 and rear portion 38.

Diaper 50 comprises a liquid-impermeable outer first cover 42 as a first thin-section element of sheet material, a liquid-permeable body-side liner 44 as a second thin-section element, and an liquid-absorbent core 46 between the outer cover and the body side liner. Additionally, side edges are given the reference number 32, leg elastic is given the reference number 40, and the diaper ear has a reference number 48.

Figure 6:
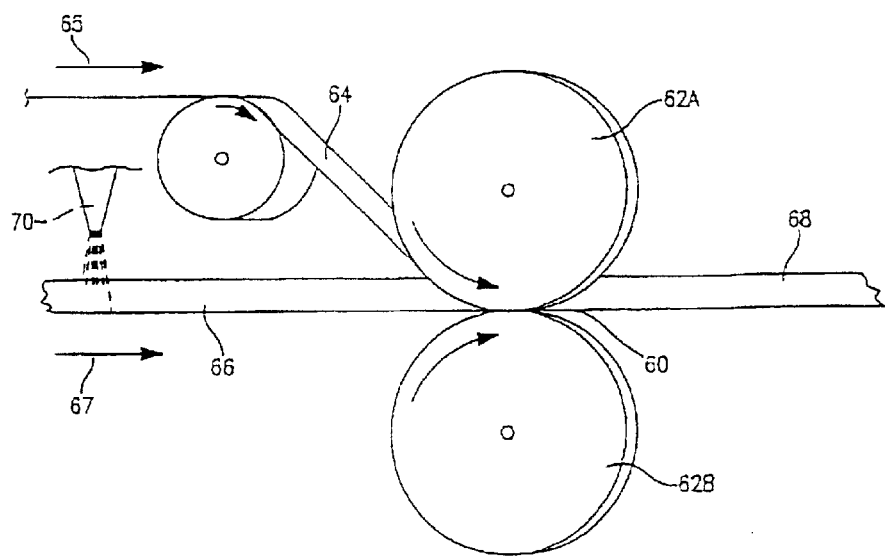
FIG. 6 shows a representative pictorial side elevation of a bonding nip such as can be used in continuous bonding processes employing bond patterns of the invention.

FIG. 6 represents a side pictorial view of bonding nip 60 such as can be used in continuous bonding processes employing, bond patterns of the invention. Bonding nip 60 is formed between two rotating rolls 62A, 62B. Rolls 62A, 62B can be mounted at any angular orientation, each with respect to the other, so long as energy can be effectively transmitted from at least one of the rolls to the material being worked in nip 60. In FIG. 6, rolls 62A, 62B are mounted such that roll 62A is positioned vertically over roll 62B. To create the bond pattern of the invention, a first web of sheet material 64 and a second web of sheet material 66 are fed from left to right in FIG. 6 as indicated by arrows 65, 67, and are urged toward each other in face-to-face relationship, in the bonding nip 60 of the machine shown in FIG. 6, to form an array of separate, distinct, and spaced elongate bond elements affixing the first and second thin-section sheet materials to each other.

The bond elements described herein and illustrated in the drawings are formed by, among other steps, pressing e.g. webs 64 and 66 against each other in nip 60 in order to activate a desired form of adhesion. Typically, one of the rolls, e.g. roll 62A, has a generally smooth outer circumferential surface while the other roll, e.g. roll 62B, bears a pattern of raised bonding protrusions, also called lands, corresponding in design and location to the bond pattern reflected in e.g. FIGS. 1A, 1B, and 1C. While the outer surface of e.g. roll 62A can bear indentations complementing the protrusions, such is not preferred. As webs 64, 66 pass through the nip, rolls 62A, 62B in combination apply pressure to the webs at locations on the webs corresponding to the respective protrusions, thereby activating the adhesive response at e.g. bond elements 12, 13, and 14.

The protrusions, which are shaped like respective bond elements, extend from a base surface on the outer circumference of roll 62B. The protrusions terminate at distal land surfaces which are responsible for creating the respective bond elements. Typical such protrusions can be, for example, up to approximately 0.10 inch in height, and up to about 0.06 inch in width. Height is defined as the dimension of the protrusion from the base circumferential surface of the roll to the distal tip, or land, which actually interfaces with e.g. the web material in which bonds are being formed. The sides of the protrusions typically extend from the base circumferential surface of the roll at angles of, for example, about 5 degrees to about 60 degrees, more preferably, about 10 degrees to about 50 degrees, to an angle perpendicular to the base circumferential surface at the respective locus on the surface of the anvil roll.

The bond pattern, as well as the individual bond elements, can be activated by a variety of methods including but not limited to applying pressure, thermal energy and pressure, or ultrasonic-frequency energy and pressure, to the workpiece in bonding nip 60. The workpiece defined for this illustration can include one or more of web 64, web 66, and the resultant bonded composite 68. Where ultrasonic energy is employed, the e.g. anvil roll 62B is properly sized, as known in the art, to not deleteriously interfere with the resonant frequency of the ultrasonic horn.

In the embodiment illustrated in e.g. one or more of FIGS. 1A–1C and 2A–2D, the bond pattern created by the process described and illustrated in FIG. 6 can join e.g. superposed webs at locations generally corresponding to the ultimate locations of side seams 32 in the finished absorbent article. As stated previously, such article typically comprises an assemblage of two or more layers or partial layers of different materials or can comprise two or more layers of substantially the same material, optionally along with other elements. Typical such material is a woven or non-woven fabric, or a polymer film.

As illustrated in FIG. 5, an absorbent article precursor, commonly referred to in the art as a work piece, can be defined as part of a continuously processed, continuous length, composite web of materials. As a work piece is defined, a bond pattern can be formed e.g. at side seams 32 either before or after the absorbent article is severed from the web, either as a fully finished or partially finished absorbent article.

While FIG. 6 shows only one method of implementing the bond pattern to form a bonded composite, other processes are contemplated such as creating the bond pattern using a plunge or press horn, or any other process capable of creating the bond pattern using e.g. pressure, thermal energy, or ultrasonic energy, in combination with adhesive.

While it is earlier suggested to pass the sheet materials through a separate nip between adhesive applicator 70 and nip 60, adhesion between the two sheet materials, in the stippled adhesive bonded areas 94 can, in the alternative, be developed in a separate bonding step e.g. at a bonding nip after the webs 64, 66 pass through nip 60. In some embodiments, nip 60 operates to develop both the bond elements 12, 13, 14, and adhesive bonds activated by the adherent material.

Additionally, the materials listed as possible materials capable of comprising an outer cover and a body side liner, as described in connection with FIGS. 4A and 4B are exemplary and preferred materials for use in fabricating useful products according to the invention.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

What is claimed is:

1. A method of bonding a first thin section element and a second thin-section element to each other, the method comprising:
   (a) applying an adherent material to at least one of the first and second thin-section elements over at least part of an area of the respective thin-section material which is to be bonded;
   (b) bringing the first and second thin-section elements together, including at the area to be bonded; and
   (c) applying force urging the first and second thin-section elements into bonding contact with each other including at the area to be bonded, and applying one of thermal energy or ultrasonic frequency energy to at least one of the first and second thin-section elements in the area to be bonded, thereby forming an array of elongate bond elements and activating the adherent material proximate and generally about ones of the bone elements, the array of elongate bond elements, in combination with the activated adherent material, comprising a bond pattern having a pattern length, a pattern width represented by first and second side edges of the bond pattern, and a central longitudinal axis extending through an interior portion of the bond pattern, the side edges of the bond pattern, and a corresponding bond pattern area between such side edges, being defined generally by these areas of the respective thin-section elements which participate in absorbing and dissipating, by operation of the bond pattern, stresses received into the bond pattern, the bond pattern being arranged and configured such that a side stress imposed from outside said bond pattern is preferentially directed away from the respective side edge and inwardly into said bond pattern, and is substantially dissipated on the interior portion of the bond pattern.

2. A process as in claim 1 comprising selecting, as at least one of the first thin-section element and the second thin-section element, a thin section element which comprises polymeric material selected from the group consisting of polyolefins including polyethylenes and polypropylenes, polyesters, and polyamides, and copolymers, mixtures, and blends of such polymeric materials.

3. A process as in claim 1 comprising selecting, as at least one of the first thin-section element and the second thin-section element, a thin section element which comprises a fibrous web defining a multiplicity of randomly spaced small openings extending from a major surface of the web into the interior of the web.

* * * * *